(12) United States Patent
Bronstein et al.

(10) Patent No.: US 6,602,658 B1
(45) Date of Patent: *Aug. 5, 2003

(54) MULTIPLE REPORTER GENE ASSAY (75) Inventors: Irena Y. Bronstein, Newton, MA (US); John J. Fortin, Georgetown, MA (US); Chris S. Martin, Belmont, MA (US); John C. Voyta, Sudbury, MA (US)

(73) Assignee: Tropix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/296,540

(22) Filed: Apr. 22, 1999

Related U.S. Application Data (63) Continuation of application No. 08/579,787, filed on Dec. 28, 1995.

(51) Int. Cl.[7] .............................. C12Q 1/00; C12Q 1/68
(52) U.S. Cl. ................................. 435/4; 435/6
(58) Field of Search .............................. 435/4, 6, 810, 435/1

(56) References Cited

U.S. PATENT DOCUMENTS 4,931,223 A * 6/1990 Bronstein et al. ........... 252/700
5,744,320 A   4/1998 Sherf et al. .................... 435/8

OTHER PUBLICATIONS

Journal of Bioluminescense and Chemiluminescence, vol. 5, No. 1, Jan./Mar. 1990, vol. 5 1–4 (1990), Unusual Luminescent Properties of Odd– and Even–Substituted Naphthyl–Derivatized Dioxetanes, B. Edwards, et al.

* cited by examiner

Primary Examiner—Kenneth R. Horlick
(74) Attorney, Agent, or Firm—Piper Rudnick LLP; Steven B. Kelber

(57) ABSTRACT

A method of measuring the activity of at least two reporter gene products in an aliquot of a sample extract is disclosed. The activities of a first and second reporter enzyme are quantified by measuring the light signal produced by degradation of a first substrate by the first reporter enzyme and the light signal produced by the degradation of a second substrate by a second reporter enzyme. Both quantifications are sequentially performed on the same aliquot of sample extract.

6 Claims, 3 Drawing Sheets

MULTIPLE REPORTER GENE ASSAY

This application is a Continuation of application Ser. No. 08/579,787 Filed on Dec. 28, 1995.

FIELD OF THE INVENTION

This invention relates to methods of detecting transcriptional activity in a cell using two or more reporter genes.

BACKGROUND OF THE INVENTION

Reporter gene assays are useful in the study of gene regulatory elements because reporter gene activity, i.e., production of the reporter protein, is directly proportional to transcriptional activity of the regulatory elements of the gene. A reporter gene construct for use in these assays contains one or more gene regulatory elements which are of interest, the minimal sequence requirements for transcription of a functional mRNA and the coding sequence for a reporter protein. Alam, J., et al, *Anal. Bioch.*, 188: 245–254 (1990). Analysis of constructs containing various deletions within the regulatory region enables mapping of regulatory sequences necessary for transcription and cell specific expression.

The reporter protein typically has a unique enzymatic activity or structure which enables it to be distinguished from other proteins present. The activity of the transcribed reporter protein, or quantification of the expressed protein, provides an indirect measurement of gene expression. Reporter gene assays enable the identification of sequences and factors that control gene expression at the transcriptional level. Bronstein, I., et al, *BioTechniques*, Vol. 17, No. 1, p. 172 (1994). Other uses for reporter gene assays include: identification of sequences and factors that control genes at the translational level, study of mechanisms and factors that influence and alter gene expression levels and drug screening in cell-based assays.

In single reporter gene assays with poor sensitivity it is difficult to distinguish negative results caused by the lack of expression or low level assay sensitivity. This problem can be overcome with assays of greater sensitivity. Multiple gene assays are commonly used to provide controls for efficiency of transfection. In such assays, cells are transfected with a mixture of two separate plasmids, each having a different reporter gene. The expression of one reporter gene is controlled by different regulatory regions being studied while the other reporter gene, acting as a control, is generally constitutively expressed by a standard promoter or enhancer. The activity of the experimental reporter enzyme is normalized to the activity of the control reporter enzyme.

In the known examples of assaying multiple reporter gene expression, a separate aliquot of the sample must be used in a separate assay to test for the activity of each enzyme. Alam, J., et al, *Anal. Bioch.*, 188: 245–254 (1990). The necessity of testing a separate portion for each enzyme decreases the precision of the assay and may introduce experimental errors into the results. Therefore, a multiple reporter gene assay which is sequentially performed on the same aliquot of cell extract would simplify the assay procedure and minimize experimental errors. The use of multiple reporter genes can improve the efficiency of high throughput screening for drug discovery.

To provide relevant experimental information, reporter assays must be sensitive, thus enabling the detection of low levels of reporter protein in cell lines that transfect poorly. The sensitivity of a reporter gene assay is a function of the detection method as well as reporter mRNA and protein turnover, and endogenous (background) levels of the reporter activity.

Commonly used detection techniques use isotopic, calorimetric, fluorometric or luminescent enzyme substrates and immunoassay-based procedures with isotopic or color endpoints. Many of these systems, however, have disadvantages that limit their usefulness in these assays. For example, isotopic substrates and immunoassays are limited by the cost, sensitivity and inconvenience of using radioisotopes. Fluorometric systems require external light sources which must be filtered to discriminate fluorescent signal, thereby limiting the sensitivity and increasing complexity of the detection system. Furthermore, fluorescence from endogenous source can interfere with fluorometric measurements. Colorimetric systems lack the sensitivity desired for sensitive reporter gene assays. Chemiluminescent and bioluminescent assays, on the other hand, have been found to be more rapid and sensitive than calorimetric assays and fluorometric assays. Jain, V. K. and Magrath, I. T., *Anal. Biochem.*, 199: 119–124 (1991). It would be, therefore, desirable to have a multiple reporter gene assay as aforesaid, which uses a luminescent detection system.

A number of genes are currently used as reporter genes including chloramphenicol acetyltransferase (CAT), secreted alkaline phosphatase, luciferase, β-galactosidase, β-glucuronidase, and human growth hormone, among others. Bronstein, I., et al, *Anal. Biochem.*, 219: 169–181 (1994). β-galactosidase and CAT are two of the most widely used reporter genes. See Alam, et al., 1990). β-galactosidase detection is commonly performed with calorimetric substrates which lack sensitivity. Fluorescent substrates are also used to detect β-galactosidase, however, those assays also lacks sensitivity and are limited by background autofluorescence and signal quenching. The most widely used assay for CAT is radioisotopic, exhibits only moderate sensitivity, and suffers from a narrow dynamic range. β-Glucuronidase (GUS) is a very widely used reporter gene in plant genetic research and to a lesser extent in mammalian cells. A common assay for GUS uses a fluorescent substrate, but is limited by background autofluorescence and signal quenching. Luciferase has become a more widely used reporter gene as it is quantitated using a very sensitive bioluminescent assay utilizing the substrate, luciferin.

Sensitive chemiluminescent assays, not limited to reporter gene assays, have been described using dioxetane substrates. Bronstein, U.S. Pat. No. 4,978,614, incorporated herein by reference. These dioxetane substrates emit visible light following enzyme induced degradation. Enhancement of the chemiluminescent degradation of 1,2-dioxetanes by enhancer substances comprised of certain water soluble substances, such as globular proteins that have hydrophobic regions, has been described. Voyta et al., U.S. Pat. No. 5,145,772, incorporated herein by reference. These dioxetane substrates are also used in reporter gene assays for alkaline phosphatase, β-galactosidase, and β-glucuronidase for example. See e.g., Bronstein, I., et al, *Anal. Biochem.*, 219: 169–181 (1994) and citations therein. However, no reporter gene assay using dioxetane substrates has been described in which the products of multiple reporter genes are sequentially quantitated in the same aliquot of cell extract.

Simple, rapid and highly sensitive, combined multiple reporter gene assays to detect commonly used reporter genes which do not use radioisotopes or require external light sources are highly desirable.

It is desirable to have a multiple reporter gene assay in which the reagents enhance the light signal produced by the reporter enzymes. It is also important that the signal from one reporter enzyme in a multiple reporter gene assay does not significantly interfere with the signal from the other reporter enzymes during measurement of their maximum light signal. It would be useful to have an assay which produces enhanced levels of light and therefore increases assay dynamic range and sensitivity and enables the use of a wide variety of instruments.

SUMMARY OF THE INVENTION

The method of the present invention provides a rapid, highly sensitive, non-isotopic method for sequentially detecting multiple reporter gene products in a single aliquot of cell extract. The method of the present invention comprises quantifying the activity of a first reporter enzyme by measuring the light signal produced by degradation of a substrate by the first reporter enzyme, and quantifying the activity of a second reporter enzyme by measuring the light signal produced by degradation of a second substrate by the second reporter enzyme, wherein both quantifications are sequentially performed on the same aliquot of sample extract. In one preferred embodiment, the presence of the first substrate enhances the light signal produced by degradation of a second substrate.

In preferred embodiments, the method of the present invention further comprises decreasing the light signal produced from the first reporter enzyme prior to quantifying the activity of the second reporter enzyme. Decreasing the signal from the first reporter enzyme preferably comprises substantially inactivating the first reporter enzyme or decreasing the amount of the first substrate.

In the methods of the present invention, substantially inactivating the first reporter enzyme comprises altering the pH of the aliquot, heating the aliquot to degrade the first enzyme or adding specific reagents to decrease activity of the first enzyme, such as alcohols such as isopropanol or ethanol, surfactants such as cetyl trimethyl ammonium bromide (CTAB) or substrate analogs.

In the methods of the present invention, decreasing the amount of the first substrate comprises adding an additional amount of the first enzyme sufficient to degrade the first substrate.

The reporter enzymes useful in the practice of this invention include luciferase, β-galactosidase, β-glucuronidase, alkaline phosphatase, and secreted placental alkaline phosphatase. Preferably, at least one of the first or second reporter enzymes is a hydrolytic enzyme capable of reacting with a dioxetane substrate. Useful hydrolytic enzymes include alkaline and acid phosphatases, esterases, decarboxylases, phospholipase D, β-xylosidase, β-D-fucosidase, thioglucosidase, β-D-galactosidase, α-D-galactosidase, α-D-glucosidase, β-D-glucosidase, α-D-mannosidase, β-D-mannosidase, β-D-fructofuranosidase, β-D-glucosiduronase, and trypsin. In one preferred embodiment, the first reporter enzyme is luciferase. In preferred embodiments, the second reporter enzyme comprises β-galactosidase. In one particularly preferred embodiment the first reporter enzyme is luciferase and the second reporter enzyme is β-galactosidase.

Preferably, at least one of the first or second substrates is a dioxetane. Dioxetane substrates useful in the present invention include:3-(2'-spiroadamantane)-4-methoxy-4-(3"-phosphoryloxy)phenyl-1,2-dioxetane, disodium salt (AMPPD), or disodium 3-(4-methoxyspiro[1,2-dioxetane-3, 2'(5'-chloro)-tricyclo-[3.3.1.1$^{3,7}$]decan]-4-yl]phenyl phosphate (CSPD), 3-(2'-spiroadamantane)-4-methoxy-4-(3"-β-D-galactopyranosyl)phenyl-1,2-dioxetane (AMPGD); 3-(4-methoxyspiro[1,2-dioxetane-3,2'-(5'-chloro)tricyclo [3.3.1.1$^{3,7}$]decan]-4-yl-phenyl-β-D-galactopyranoside (Galacton™), and 5-chloro-3-(methoxyspiro[1,2-dioxetane-3,2'-(5'-chloro)tricyclo[3.3.1$^{3,7}$]decan-4-yl-phenyl-β-D-galactopyranoside (Galacton-Plus).

In certain embodiments, the method further comprises adding a water soluble polymeric enhancer molecule to enhance the light signal produced by enzymatic degradation of the dioxetane. There can be one enhancer for each dioxetane or the same enhancer can be used for multiple substrates. Polymeric enhancers useful in the practice of the present invention include bovine serum albumin, human serum albumin or polymeric quaternary onium salts. The polymeric quaternary onium salts comprise poly vinylbenzyltrimethylammonium chloride (TMQ), polyvinyl benzyl tributyl ammonium chloride (TBQ), polyvinylbenzyltributylphosphonium chloride, polyvinylbenzyl benzyldimethylammonium chloride (BDMQ) or polyvinyl tributyl sulfonium chloride. Other co-polymers, such as water soluble quarternary ammonium-phosphonium, ammonium-sulfonium and. sulfonium-phosphonium polymers are also useful as enhancer molecules.

In other embodiments, these methods further comprise adding an accelerator solution prior to measuring the second enzyme activity. The accelerator solution is used to substantially inactivate the first reporter enzyme and simultaneously increase the light signal produced by the second enzyme. The accelerator solution comprises a water soluble polymeric enhancer molecule. Preferably the pH of the accelerator is from about 9 to about 12. When the accelerator is added to the aliquot of cell extract it alters the pH of the aliquot. For example, in a preferred embodiment, the accelerator solution is at a pH at about 10.8. When the accelerator is added to the aliquot it increases the pH of the aliquot from about 6.0 to greater than 9.0. The altered pH of the aliquot decreases the activity of the first reporter enzyme and activates the production of signal from accumulated enzymatic product of the degradation of the second substrate. The polymeric enhancers described in the preceding paragraph are used in the accelerator solution.

The method of this invention also provides methods of quantifying the product of more than two reporter genes by measuring multiple enzyme activities in a single aliquot of cell extract. One such method comprises (a) quantifying the activity of a first reporter enzyme in an aliquot of the cell extract by measuring the light signal produced by degradation of a first substrate; (b) quantifying the activity of a second reporter enzyme in the aliquot of the cell extract by measuring the light signal produced by degradation of a second substrate; and (c) quantifying the activity of a third reporter enzyme in the aliquot of the cell extract by measuring the light signal produced by degradation of a third substrate, wherein all quantifications are sequentially performed on the same aliquot of sample extract. In this method, the first, second and third substrates are different and at least one of the substrates is a dioxetane. In certain embodiments, the method of measuring products of more than two reporter genes further comprises decreasing the activity of the reporter enzymes prior to quantifying the activity of the subsequent reporter enzyme. For example, prior to quantifying the activity of the second reporter enzyme, the light signal generated by the first substrate for the first reporter enzyme is decreased. This method further comprises the measurement of the activity of the second reporter enzyme and then further measuring the activity of the third reporter enzyme.

The invention also provides a system for detecting the products of more than one reporter gene in an aliquot of a sample extract, the system comprising: the reagents for quantifying each of two or more reporter enzymes; the substrates for each of the reporter enzymes, wherein at least one of the substrates is a dioxetane; and an accelerator solution containing a water soluble polymeric enhancer molecule. The accelerator solution comprises a water soluble polymeric enhancer molecule at a pH from about 9 to about 12, to induce the signal produced from the second or a third reporter enzyme-substrate reaction and decrease the activity of the first reporter enzyme. The polymeric enhancer comprises bovine serum albumin, human serum albumin or polymeric quaternary ammonium, sulfonium and phosphonium salts. The polymeric quaternary ammonium, sulfonium and phosphonium salts comprise polyvinylbenzyltrimethylammonium chloride (TMQ), polyvinylbenzyltributylammonium chloride (TBQ), polyvinylbenzyl benzyldimethylammonium chloride (BDMQ) polyvinylbenzylsulfonium chlroide or polyvinylbenzyl tributylphosphonium chloride. Other co-polymers, such as ammonium-phosphonium, ammonium-sulfonium and sulfonium-phosphonium quarternary polymers are also useful as enhancer molecules.

One preferred embodiment of the invention provides a method of measuring the products of more than one reporter gene in an aliquot of a sample extract. The method comprises: (a) adding a first substrate which is the substrate of a first reporter enzyme product and a second substrate which is the substrate of a second reporter enzyme product to an aliquot of the cell extract, the first substrate comprising luciferin for detection of the first enzyme luciferase and the second substrate comprising a dioxetane and the second enzyme being a hydrolytic enzyme; (b) measuring the activity of the first reporter enzyme; (c) adding an accelerator solution which substantially inactivates the first reporter enzyme and simultaneously increases the chemiluminescent signal produced from the degraded substrate for the second reporter enzyme by increasing the pH of the aliquot, and (d) measuring the chemiluminescent signal produced from the degraded substrate for the second reporter enzyme in the same aliquot of the cell extract, wherein the presence of the first substrate enhances the light signal produced by degradation of a second substrate. In one preferred embodiment, the first reporter enzyme is luciferase and the second reporter enzyme is β-galactosidase.

The present invention provides a method of detecting the activity of a first and second reporter enzyme sequentially in the same aliquot of cell extract sample rather than using separate aliquots of the cell extract to individually measure each enzyme as has been previously performed in the art. The method of the present invention therefore decreases the likelihood of experimental error, thus enabling more reliable data.

DETAILED DESCRIPTION OF THE INVENTION

The method of the present invention provides a rapid, highly sensitive, non-isotopic method for sequentially detecting multiple reporter gene activity in a single aliquot of cell extract sample. The method of the present invention is particularly useful in measuring transcriptional activity of cells transfected with more than one reporter gene. Transfection of these cells is accomplished by methods known in the art. See e.g., Alam, J. and Cook, J. L., *Anal. Bioch.* 188: 245–254 (1990). Typically, cells are co-transfected with a DNA mixture of two separate plasmids, each having a different reporter gene. One plasmid has a reporter gene the expression of which is regulated by a known control promoter. This reporter gene acts as a control. The second plasmid has a second reporter gene the expression of which is controlled by the regulatory region being studied. Transcription of each reporter gene is analyzed by measuring the activity of its product, a "reporter enzyme". The activity of the second reporter enzyme is typically normalized to the activity of the first reporter enzyme. Id at 249.

In one embodiment, the method of the present invention for measuring the activity of more than one reporter gene product in an aliquot of sample extract comprises the steps of: (a) quantifying the activity of a first reporter enzyme by measuring the light signal produced from degradation of a first substrate by the first reporter enzyme; and (b) quantifying the activity of a second reporter enzyme by measuring the light signal produced from degradation of a second substrate by a second enzyme, wherein both quantifications are sequentially performed on the same aliquot of sample extract. The intensity of the luminescent signal produced from the substrates is a function of the activity of the enzyme, i.e., the effectiveness of the enzyme in terms of its ability to degrade its substrate.

The first and second reporter enzymes useful in the present invention comprise any protein produced from any gene that exhibits enzymatic activity and degrades a substrate to produce a light signal. Examples of such enzymes include luciferase, alkaline phosphatase, β-galactosidase, β-glucuronidase, carboxylesterase, lipases, phospholipases, sulphatases, ureases peptidases, proteases and others. Further, in preferred embodiments, at least one of the reporter enzymes is a hydrolytic enzyme. In some of these embodiments, it is preferred that the second reporter enzyme is the hydrolytic enzyme. In other embodiments, both enzymes are hydrolytic and can be selected from alkaline and acid phosphatases, esterases, decarboxylases, phospholipase D, β-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, β-D-glucosiduronase, and trypsin.

In the method of the present invention, the substrates for the reporter enzymes comprise any luminescent substrate capable of producing a light signal. Preferably, the first substrate is different from the second substrate and at least one substrate is a dioxetane. Dioxetanes are molecules that have a 4-membered ring in which 2 of the members are adjacent oxygen atoms. Dioxetanes can be thermally, chemically or photochemically decomposed to form carbonyl products, e.g., esters, ketones or aldehydes. Release of energy in the form of light (i.e., luminescence) accompanies the decompositions. The dioxetane substrate contains an enzyme-cleavable group which can be cleaved by a corresponding enzyme. The reporter enzyme cleaves this enzyme-cleavable group from the substrate to form a negatively charged group (e.g., an oxygen anion) bonded to the dioxetane. This dioxetane anion decomposes to form a luminescent substance which produces light. The light signal is detected as an indication of the presence and the amount of the enzyme. By measuring the intensity of the luminescence, the concentration of the reporter enzyme can be determined.

In one preferred embodiment, the dioxetane-containing substrate preferably has the formula (I)

where T is a substituted (i.e. containing one or more $C_1$–$C_7$ alkyl groups or heteroatom groups, e.g. halogens) or unsubstituted cycloalkyl ring (having between 6 and 12 carbon atoms, inclusive, in the ring) or polycycloalkyl group (having 2 or more fused rings, each ring independently having between 5 and 12 carbon atoms, inclusive), bonded to the 4-membered dioxetane ring by a Spiro linkage, e.g., a chloroadamantyl or an adamantyl group, most preferably chloroadamantyl; Y is a fluorescent chromophore, (i.e. Y is a group capable of absorbing energy to form an excited, i.e. higher energy, state, from which it emits light to return to its original energy state); X is hydrogen, a straight or branched chain alkyl or heteroalkyl group (having between 1 and 7 carbon atoms, inclusive, e.g., methoxy, trifluoromethoxy, hydroxyethyl, trifluoroethoxy or hydroxypropyl), an aryl group (having at least 1 ring e.g., phenyl), a heteroaryl group (having at least 1 ring e.g., pyrrolyl or pyrazolyl), a heteroalkyl group (having between 2 and 7 carbon atoms, inclusive, in the ring, e.g., dioxane), an aralkyl group (having at least 1 ring e.g., benzyl), an alkaryl group (having at least 1 ring e.g., tolyl), or an enzyme-cleavable group i.e., a group having a moiety which can be cleaved by an enzyme to yield an electron-rich group bonded to the dioxetane, e.g., phosphate, where a phosphorus-oxygen bond can be cleaved by an enzyme, e.g., acid phosphatase or alkaline phosphatase, to yield a negatively charged oxygen bonded to the dioxetane or OR; and Z is hydrogen, hydroxyl, or an enzyme-cleavable group (as defined above), provided that at least one of X or Z must be an enzyme-cleavable group, so that the reporter enzyme cleaves the enzyme-cleavable group which leads to the formation of a negatively charged group (e.g., an oxygen anion) bonded to the dioxetane, the negatively charged group causing the dioxetane to decompose to form a luminescing substance (i.e., a substance that emits energy in the form of light) that includes group Y. The luminescent signal is detected as an indication of the activity of the reporter enzyme. By measuring the intensity of luminescence, the activity of the reporter enzyme can be determined.

When X, in formula I, is OR, moiety R is a straight or branched alkyl, aryl, cycloalkyl or arylalkyl of 1–20 carbon atoms. R may include 1 or 2 heteroatoms which may be P, N, S or O. The substituent R is halogenated. The degree of halogenation will vary depending on the selection of substituents on the adamantyl group, on the aryl group, and the desired enzyme kinetics for the particular application envisioned. Most preferably, R is a trihaloalkyl moiety. Preferred groups include trihalo lower alkyls, including trifluoroethyl, trifluoropropyl, heptafluoro butyrol, hexafluoro-2-propyl, α-trifluoromethyl benzyl, α-trifluoromethyl ethyl and difluorochloro butyl moieties. The carbon atoms of substituent R may be partially or fully substituted with halogens. When R is aryl, preferred groups may include a phenyl ring substituted with one or more chloro, fluoro, or trifluoromethyl groups, e.g., 2,5-dichlorophenyl, 2,4-difluorophenyl, 2,3,5-trifluorophenyl, 2-chloro-4-fluorophenyl or 3-trifluoromethyl phenyl. Fluorine and chlorine are particularly preferred substituents, although bromine and iodine may be employed in special circumstances.

Group Y is a fluorescent chromophore or fluorophore bonded to enzyme-cleavable group Z. Y becomes luminescent upon the dioxetane decomposition when the reporter enzyme cleaves group Z, thereby creating a electron-rich moiety which destabilizes the dioxetane, causing the dioxetane to decompose. Decomposition produces two individual carbonyl compounds, one of which contains group T, and the other of which contains groups X and Y. The energy released from dioxetane decomposition causes compounds containing the X and the Y groups to luminesce (if group X is hydrogen, an aldehyde is produced). Y preferably is phenyl or aryl. The aryl moiety bears group Z, as in formula I, and additionally 1–3 electron active groups, such as chlorine or methoxy, as described in U.S. patent application Ser. No. 08/231,673 filed Apr. 25, 1994.

Any chromophore can be used as Y. In general, it is desirable to use a chromophore which maximizes the quantum yield in order to increase sensitivity. Therefore, Y usually contains aromatic groups. Examples of suitable chromophores are further detailed in U.S. Pat. No. 4,978,614.

Group Z bonded to chromophore Y is an enzyme cleavable group. Upon contact with an enzyme, the enzyme-cleavable group is cleaved yielding an electron-rich moiety bonded to a chromophore Y; this moiety initiates the decomposition of the dioxetane into two individual carbonyl containing compounds e.g., into a ketone or an ester and an aldehyde if group X is hydrogen. Examples of electron-rich moieties include oxygen, sulfur, and amine or amino anions. The most preferred moiety is an oxygen anion. Examples of suitable Z groups, and the enzymes specific to these groups are given in Table 1 of U.S. Pat. No. 4,978,614. Such enzymes include alkaline and acid phosphatases, esterases, decarboxylases, phospholipase D, β-xylosidase, β-D-fucosidase, thioglucosidase, β-D-galactosidase, α-D-galactosidase, α-D-glucosidase, β-D-glucosidase, β-D-glucouronidase α-D-mannosidase, β-D-mannosidase, β-D-fructofuranosidase, β-D-glucosiduronase, and trypsin.

Dioxetane may also contain one or more solubilizing substituents attached to any of the T, Y and X, i.e., substituents which enhance the solubility of the dioxetane in aqueous solution. Examples of solubilizing substituents include carboxylic acids, e.g., acetic acid; sulfonic acids, e.g., methanesulfonic acid; and quaternary amino salts, e.g., ammonium bromide; the most preferred solubilizing substituent is methane or ethanesulfonic acid.

Other dioxetanes useful in the practice of this invention are described in U.S. Pat. No. 5,089,630; U.S. Pat. No. 5,112,960; U.S. patent application Ser. No. 057,903 filed May 7, 1993, U.S. Pat. No. 5,538,847 and U.S. patent application Ser. No. 08/231,673 filed Apr. 25, 1994, U.S. Pat. No. 5,582,980.

For assays using alkaline phosphatase or secreted human placental alkaline phosphatase (SEAP) as a reporter enzyme, the substrate for that enzyme preferably comprises a phosphate-containing dioxetane, such as 3-(2'-spiroadamantane) -4-methoxy-4-(3"-phosphoryloxy) phenyl-1,2-dioxetane, disodium salt (AMPPD), or disodium 3-(4-methoxyspiro[1,2-dioxetane-3,2'(5'-chloro)-tricyclo-[3.3.1.1$^{3,7}$]decan]-4-yl]phenyl phosphate (CSPD), respectively.

For assays using β-galactosidase as a reporter enzyme, the substrate preferably comprises a dioxetane containing galactosidase-cleavable or galactopyranoside groups. When using βgalactosidase, the luminescence results from the enzymatic cleavage of the sugar moiety from the dioxetane substrate. An example of such a substrate is 3-(2'-spiroadamantane)-4-methoxy-4-(3"-β-D-galactopyranosyl) phenyl-1,2-dioxetane (AMPGD), 3-(4-methoxyspiro[1, 2-dioxetane-3,2'-(5'-chloro)tricyclo[3.3.1.1$^{3,7}$]-decan]-4-yl-phenyl-β-D-galactopyranoside (Galacton™), and 5-chloro-3-(methoxyspiro[1,2-dioxetane-3,2'-(5'-chloro)tricyclo [3.3.1.$^{3,7}$]decan-4-yl-phenyl-β-D-galactopyranoside (Galacton-Plus™).

For assays using β-glucuronidase as a reporter enzyme, the substrate comprises a dioxetane containing β-glucuronidase-cleavable groups such as a glucuronide. For assays using carboxyl esterase, the enzyme cleaves the ester group of the dioxetane. For assays using proteases and phospholipases, the enzymes cleave a suitable enzyme-cleavable group bound to the dioxetane.

In preferred embodiments of the assay of the present invention, the first and second substrates are both present in the aliquot during quantification of the activity of the first reporter enzyme. In these embodiments, the presence of the second reporter enzyme, as well as its substrate, does not interfere with the activity of the first reporter enzyme or measurement of the light signal produced by degradation of the first substrate by the first reporter enzyme. In one preferred embodiment, light produced by degradation of the first substrate occurs at a pH at which the product of the degradation of the second substrate does not produce light, or the second enzyme is not active during the first measurement. In one such embodiment, the product of enzymatic reaction with the second substrate does not generate a measurable signal during the first quantification because the environment of the aliquot inhibits light production by the product of this second enzymatic reaction. For example, the measurement of light production by the degradation of the first substrate preferably occurs at a neutral pH. The second reporter enzyme also acts on its substrate during this time, however, at this pH, no significant production of light from this reaction occurs. It is preferable to allow a predetermined period of time to elapse prior to increasing the pH and measuring light production of the second enzymatic reaction to allow the product of that reaction to accumulate, thereby producing a more intense light signal.

In other embodiments of the present invention, the presence of the second reporter enzyme in the aliquot does not interfere with the activity of the first reporter enzyme or measurement of the light signal produced by that first enzyme. In these embodiments, the method further comprises increasing the enzymatic activity of the second reporter enzyme subsequent to quantifying the activity of the first enzyme. This can be readily accomplished by methods known in the art to activate enzyme activity. In especially preferred embodiments, the pH of the aliquot is adjusted to create an environment in which the second enzyme is active prior to the second quantification. For example, in some embodiments, using alkaline phosphatase as the second reporter enzyme, the pH of the aliquot is raised because, the activity of alkaline phosphatase is increased at alkaline pH.

In other embodiments, the presence of the second enzyme does not interfere with the measurement of the light signal from the first substrate, because the substrate of the second enzyme is absent from the aliquot during this measurement. In such embodiments, the second enzyme is active but there is no substrate on which it can act. In one preferred embodiment, the activity of the second reporter enzyme is induced by the addition of the second substrate after decreasing the activity of the first reporter enzyme or after reduction in the signal produced by the first enzymatic reaction. For example, in an assay using β-galactosidase as the first reporter enzyme and alkaline phosphatase as the second reporter enzyme, light production as a result of the β-galactosidase reaction is optimized at a higher than neutral pH. However, the increased pH simultaneously activates the second reporter enzyme, alkaline phosphatase, which could produce light which would interfere with the quantification of the activity of the first reporter enzyme. In such an assay, it is preferred that the second substrate is added subsequent to the first quantification and most preferably, after that light signal has abated. This addition is readily accomplished and is especially easy when using a detection device which has an injector system as is known in the art.

The light signal produced by the degradation of the first substrate by the first reporter enzyme does not interfere with the quantification of the light signal produced by the second reporter enzyme. This is accomplished in preferred embodiments by decreasing the signal produced by the substrate for the first reporter enzyme after measuring the light signal produced by degradation of the first substrate and prior to quantifying the activity of the second reporter enzyme.

In some preferred embodiments, the signal produced from the substrate for the first reporter enzyme is decreased by substantially inactivating the first reporter enzyme. Methods of substantially inactivating the first reporter enzyme are known in the art. However, these methods must not interfere with measurement of the second enzyme product activity. In one preferred method of this invention, the first reporter enzyme is substantially inactivated by altering the pH of the aliquot. The pH can be altered by adding acids or bases to the aliquot, depending on the enzyme, to provide an environment which is inhospitable to the first enzyme. Preferably the pH of the aliquot is increased. This inactivates the first enzyme, preventing it from further degrading its substrate and producing a light signal. In another embodiment, the aliquot is heated to degrade the first enzyme or specific inhibitors can be added. Examples of inhibitors include alcohols such as isopropanol or ethanol, surfactants such as cetyl trimethyl ammonium bromide (CTAB) or substrate analogs which bind to, and inactivate the enzyme.

In other embodiments, the signal produced by the substrate for the first enzyme is decreased by decreasing the amount of the first substrate. The appropriate method can be chosen by one skilled in the art based upon the specific enzyme and substrate used. However, in one such embodiment, the substrate concentration is preferably decreased by adding an additional amount of the first enzyme sufficient to degrade the residual first substrate remaining after quantification of the first reporter enzyme. For example, after measuring the light signal produced from the degradation of the first substrate by the first enzyme, e.g., alkaline phosphatase, an amount of alkaline phosphatase is added to the aliquot sufficient to degrade any residual substrate and to prevent any potentially interfering light signal. Since the second substrate is unique to the second reporter enzyme, the presence of the first enzyme in excess will not interfere with the detection of the second light signal. This is useful when dioxetane substrates are used for both the first and second reporter enzymes.

In another embodiment, decreasing the amount of the first substrate comprises heating the aliquot to degrade the first substrate. Heat inactivation is preferably utilized in embodiments in which the second substrate is added subsequent to inactivation of the first substrate.

Figure 1:
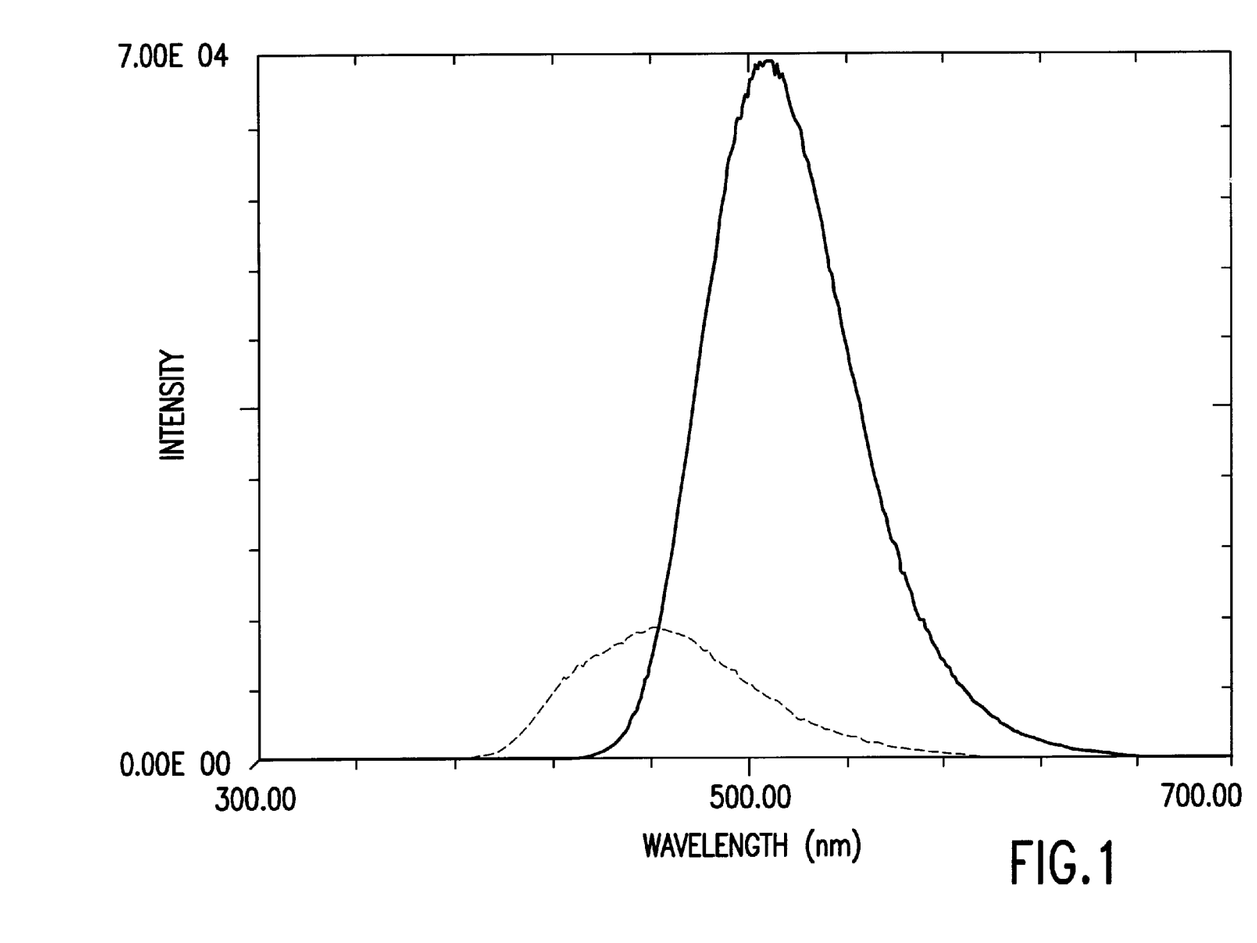
FIG. 1 shows the enhanced signal produced by β-galactosidase in the presence of luciferin.

In certain embodiments of the present invention, the presence of the first substrate enhances the light signal produced by degradation of the second substrate. This enhanced signal provides a more sensitive assay. Although the inventors do not intend to be bound by theory, it is believed that the energy produced by the degradation of the second substrate is transferred to the remaining first substrate, thereby enhancing the intensity of the light signal produced. In one preferred embodiment of this method, the first substrate is luciferin. In this embodiment the second substrate is preferably a dioxetane substrate. It is believed that luciferin is a very efficient energy acceptor and emits a light signal as a result of energy transfer from the excited state generated from the dioxetane decomposition. This produces greater signal intensity. FIG. 1 shows the enhanced signal produced by 5-chloro-3-(methoxyspiro[1,2-dioxetane-3,2'-(5'-chloro)tricyclo[$3.3.1^{3,7}$]decan-4-yl-phenyl-β-D-galactopyranoside reaction with β-galactosidase in the presence of luciferin (solid line) compared to the same reaction in the absence of luciferin (dotted line). This enhanced signal provides a highly sensitive assay enabling the detection of β-galactosidase in the 8 fg to 20 ng range.

Certain preferred embodiments of the present invention further comprise adding a water soluble enhancer molecule which enhances the light signal produced from the enzymatic degradation of dioxetane substrates by the reporter enzymes.

Certain water soluble naturally-occurring and synthetic substances, generally macromolecular in nature, enhance the chemiluminescent signal intensity in part by providing a hydrophobic environment. These substances, for example water soluble globular proteins that contain hydrophobic regions: mammalian serum albumins such as bovine serum albumin (BSA) and human serum albumin (HSA), or water soluble polymeric quaternary onium salts: polyvinylbenzyl-trimethylammonium chloride (TMQ) or polyvinylbenzyl-benzyldimethylammonium chloride (BDMQ), and polyvinylbenzyltributyl phosphonium chloride increase the chemiluminescent signal intensity produced by the decomposition of enzymatically cleavable 1,2-dioxetanes in aqueous solutions. Co-polymers, such as water soluble quaternary ammonium-phosphonium, ammonium-sulfonium and sulfonium-phosphonium polymers are useful as enhancer molecules.

By virtue of the presence of effective amounts of an enhancer substance or substances the intensity of the light emitted in aqueous medium is increased significantly as compared to the intensity of light emitted in the absence of such enhancers. These compounds enhance the intensity of the chemiluminescent signal from 1,2-dioxetanes by a factor of at least 10%, but usually at least tenfold and oftentimes by factors of at least 100 to 1,000,000.

Included among such enhancer substances are macromolecular globular proteins, generally ones having molecular weights ranging from about 1000 to about 600,000 daltons, as determined by SDS gel electrophoresis, that include hydrophobic regions: mammalian serum albumins such as BSA, HSA and the like; globular proteins such as mammalian IgG, IgE, Protein A, avidins, and the like; serum lipoproteins, apolipoproteins, and the like.

Synthetic oligomeric or polymeric enhancer substances that can be used in practicing this invention include, first of all, water soluble polyvinylaryl quaternary onium salts, such as the polyvinylbenzyl quaternary ammonium, sulfonium and phosphonium salts having the formula:

where $E^+$ can be P, N or S.

In this formula each of $R_1$, $R_2$ and $R_3$ can be a straight or branched chain unsubstituted alkyl group having from 1 to 20 carbon atoms, inclusive, e.g., benzyl, methyl, ethyl, n-butyl, t-butyl, cetyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amino, e.g., acetamido or cholesteryloxycarbonylamido, or fluoroalkane or fluoroaryl, e.g., heptafluorobutyl, groups, an unsubstituted monocycloalkyl group having from 3 to 12 ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in toto, unsubstituted or substituted with one or more alkyl, aryl, or fluoroalkane or fluoroaryl groups, e.g., phenyl, naphthyl, pentafluorophenyl, ethylphenyl, benzyl, hydroxybenzyl, phenylbenzyl or dehydroabietyl; at least two of $R_1$, $R_2$ and $R_3$, together with the quaternary atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoanylated, e.g., 1-pyridyl, 1-(3 alkyl or aralkyl)imidazolium, morpholino, piperidino or acylpiperidino, benzoxazole, benzthiazole or benzamidazole.

The symbol $X^-$ represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), lucifer yellow CH and diphenilanthracenesulfonate, perchlorate, alkanoate, e.g., acetate, arylcarboxylate, e.g., fluorescein or fluorescein derivatives, benzoheterocyclicarylcarboxylate, e.g., 7-diethylamino-4-cyanocoumarin-3-carboxylate, or substituted monoaryloxyphosphate, e.g., a 3-(2'-spiroadamantane)-4-methoxy-(3"-phosphoryloxy)phenyl-1,2-dioxetane dianion or other dianions indicated in formula (I), supra.

The symbol n represents a number such that the molecular weight of such poly vinylbenzyl quaternary onium salts will range from about 800 to about 200,000, and preferably from about 20,000 to about 70,000, as determined by intrinsic viscosity or LALLS techniques.

Illustrative of such water soluble poly(vinylbenzyl quaternary ammonium salts) are TMQ, BDMQ, and the like.

Water soluble acetals of a polyvinylalcohol and a formylbenzyl quaternary onium salt, having the formula:

(VII)

wherein E+ can be P, N or S and each $R_4$ is the same or a different aliphatic substituent and $X_1$ is an anion, as disclosed and claimed in Bronstein-Bonte et al. U.S. Pat. No. 4,124,388 can also be used as enhancer substances in practicing this invention. And, the individual vinylbenzyl quaternary onium salt monomers used to prepare the poly vinylbenzyl quaternary onium salts of formula II above can also be copolymerized with other vinylbenzyl quaternary onium salt monomers whose polymers are depicted in formula II, or with other ethylenicaly unsaturated monomers having no quaternary onium functionality, to give polymers such as those disclosed and claimed in Land et al. U.S. Pat. No. 4,322,489; Bronstein-Bonte et al. U.S. Pat. No. 4,340,522, Land et al. U.S. Pat. No. 4,424,326; Bronstein-Bonte et al. U.S. Pat. No. 4,503,138 and Bronstein-Bonte U.S. Pat. No. 4,563,411, all of which polymers can also be used as enhancer substances in practicing this invention. Preferably these quaternized polymers will have molecular weights within the ranges given above for the polyvinylbenzyl quaternary ammonium salts of formula II.

Other water soluble oligomeric, homopolymeric and copolymeric materials can be used as enhancer substances in addition to or instead of the foregoing polymers and are further described in U.S. Pat. No. 5,145,772.

The amount of enhancer substance used varies depending on the particular enhancer chosen and the amount and type of chemiluminescent compounds present. The necessary amount can be readily determined by one skilled in the art based upon the present teachings. Furthermore, the disclosure contained within U.S. Pat. No. 5,145,772 would assist one skilled in the art in practicing this invention.

The enhancer molecule can be added at any point during the method of the present invention. If the first substrate, but not the second, is a dioxetane, the enhancer is preferably added prior to or simultaneous to quantification of the first reporter enzyme. If the second substrate, but not the first, is a dioxetane, the enhancer is added at any time, but preferably subsequent to quantification of the first reporter enzyme and prior or simultaneous to quantification of the second reporter enzyme. If both the first and second substrates are dioxetanes, the enhancer molecule is preferably added prior to any quantification or simultaneous to the first. In this last embodiment, one enhancer can be used to enhance the light signals produced by decomposition of both substrates. Or alternatively, a different enhancer is used for each substrate.

In some embodiments there is an incubation period subsequent to quantification of the light signal produced by the substrate for the first enzymes, in part, to allow for the light signal produced by the first substrate to diminish. The length of the incubation period will depend on the concentration of the first reporter enzyme and the half-life of the light signal produced by the substrate. If the first reporter is present in high concentrations, it may interfere with the quantification of low levels of the subsequent reporter enzymes. A longer incubation period will decrease the residual light signal from the substrate for the first reporter enzyme. The incubation period is preferably 10 to 120 minutes, more preferably 20 to 90 minutes, and most preferably 30 to 60 minutes. Taking into account the teachings of the present invention the appropriate length of the incubation period can readily be determined by one skilled in the art. Regardless of the incubation time period selected, the timing of the addition of the accelerator and measurement of the signal produced by the second reporter enzyme after addition of the accelerator must be held constant throughout the assay.

The present invention provides a method of measuring the activity of more than two reporter gene products. In one preferred embodiment, this method comprises first quantifying the activity of a first reporter enzyme in an aliquot of the cell extract by measuring the light signal produced by degradation of a first substrate and then decreasing the activity of the first reporter enzyme. The method also comprises quantifying the activity of a second reporter enzyme in the aliquot of the cell extract by measuring the light signal produced by degradation of a second substrate. The method further comprises quantifying the activity of a third reporter enzyme in the aliquot of the cell extract by measuring the light signal produced by degradation of a third substrate. All quantifications are sequentially performed on the same aliquot of sample extract.

The method of the present invention may be performed in any luminometer, preferably luminometers with automatic injectors, or other instrumentation which enables the measurement of light emission. The method is also useful in a luminometer equipped with a single injector. However, when using a single injector it is preferred that the injector is rinsed thoroughly between injection of the second buffer and the accelerator. The method can be performed using manual injection if the light signal of each sample is measured after approximately the same time interval subsequent to the addition of the accelerator to the samples.

A number of factors determine the volume of the aliquot of cell extract used, such as, the availability of the sample, instrumentation and availability of reagent. Preferably, the volume of the aliquot of cell extract used ranges from 1 to 100 $\mu$L, more preferably 2 to 20 $\mu$L, and most preferably from about 2 to 10 $\mu$L. The lysis solution used to lyse transfected cells to obtain the cell extract can be any lysis solution known in the art.

The method of this invention is highly sensitive and detects from about 1 fg to 20 ng of purified luciferase, 10 fg to 20 ng of purified β-galactosidase, 2 fg to 100 ng of purified alkaline phosphatase, and 10 fg to 100 ng of purified β-glucuronidase.

In one preferred embodiment, the activity of more than one reporter gene product in an aliquot of a sample extract is measured by adding a first substrate which is the substrate for a first reporter enzyme and a second substrate which is the substrate for a second reporter enzyme to an aliquot of the cell extract. In this preferred embodiment, the first enzyme is a luciferase, the second enzyme is a hydrolytic enzyme, the first substrate is luciferin and the second substrate is a dioxetane. The second reporter enzyme is preferably selected from β-galactosidase, β-glucuronidase, alkaline phosphatase and carboxyl esterase. In a preferred embodiment the second reporter enzyme is β-galactosidase. In this embodiment, the method comprises adding the substrate for the first enzyme at the same time as the substrate for the second enzyme and measuring the chemiluminescent signal for the first reporter enzyme by measuring the light signal produced from luciferase-luciferin reaction and simutaneously adding the substrate for the second enzyme. Then the method comprises adding an accelerator solution which substantially inactivates the first reporter enzyme by increasing the pH of the aliquot. The increased pH of the aliquot also activates the light production from the accumulated product of the second reporter enzyme-second substrate reaction. The accelerator solution also includes an enhancer, such as polyvinylbenzyltributyl ammonium chloride, which, as aforesaid, enhances the light signal produced by decomposition of the dioxetane substrate for the second reporter enzyme. The activity of the second reporter enzyme is then measured by reading the chemiluminescent signal intensity in the same aliquot of the cell extract. In embodiments where luciferin is used as the first substrate, the presence of this substrate further enhances the light signal produced by the second substrate.

The method of the present invention also provides a kit for detecting the transcriptional activity of more than one reporter gene in an aliquot of a sample extract. Such a kit comprises the reagents for quantifying each of two or more reporter enzymes and the substrates for each of the reporter enzymes, wherein at least one of the substrates is a dioxetane. The kit also comprises an accelerator solution containing a water soluble polymeric enhancer molecule optionally the accelerator solution comprises a water soluble polymeric enhancer molecule at a pH from about 9 to about 14, to raise the pH, decrease the activity of the first reporter enzyme and increase the signal produced from the enzymatic degradation of the second substrate by the second reporter enzyme. The polymeric enhancer preferably comprises bovine serum albumin, human serum albumin or polymeric quaternary onium salts. The polymeric quaternary onium salts preferably comprise polyvinylbenzyltrimethylammonium chloride (TMQ), polyvinylbenzyltributylammonium chloride (TBQ), polyvinylbenzyl benzyldimethylammonium chloride (BDMQ) or polyvinylbenzyltributyl phosphonium chloride.

The following examples are provided to illustrate the present invention and are not intended in any way to limit the scope of the invention.

EXAMPLE I

Preparation of Samples

Routes

A. Preparation of Cell Extracts From Tissue Culture Cells:

The lysis solution contained 100 mM potassium phosphate pH 7.8, 0.2% Triton X-100 and stored at 4° C. Dithiothrietol (DTT) was added fresh prior to use to a final concentration of 0.5 mM. The cells were rinsed twice with 1×phosphate buffered saline (PBS) containing: 0.058 $Na_2HPO_4$, 0.017M $NaH_2PO_4$, 0.068M NaCl at pH 7.3.

Lysis solution was added to cover cells. For example, 250 $\mu$L of lysis buffer was adequate for a 60 mm culture plate. The cells were detached from culture plate using a rubber policeman or equivalent. Non-adherent cells were pelleted and sufficient lysis buffer added to cover the cells. The cells were then resuspended in the lysis buffer by pipetting.

The lysed cells were then transferred to a microfuge tube and centrifuged for 2 minutes to pellet any debris. The supernatant was then transferred to a fresh microfuge tube. The cell extracts were either used immediately or frozen at $-70°$ C. for future use.

B. Preparation of Purified Enzymes

Purified luciferase (Analytical Luminescence Laboratories, Ann Arbor, Mich.) and β-galactosidase (G-5635, Sigma, ST. Louis, Mo.) were individually diluted in lysis solution (0.1 M potassium phosphate, pH 7.8, 0.2% Triton X-100) containing 0.5 mM DTT 1 mg/ml BSA Fraction V (Sigma A 3059).

EXAMPLE II

Chemiluminescent Assay Procedure for Luciferase and β-Galactosidase Resorter Enzymes All assays were run in triplicate. Buffer A was prepared from lyophilized pH 7.8 solution containing 75 mM Tricine-Cl pH 7.8, 50 mM $MgSO_4$, 7.5 mM ATP, 1.25 mM pyrophosphate, 4 mM EDTA and 1 mg/ml bovine serum albumin (BSA). The lyophilized solution was reconstituted in 5 mL of sterile deionized or Milli-Q water. The lyophilized solution was stored at $-20°$ C. before reconstitution.

Buffer B was prepared from a lyophilized solution of 0.625 mM luciferin and 5 mM Tris acetate pH 6.5 reconstituted in 20 mL of sterile deionized or Milli-Q water. The β-galactosidase substrate containing 1.34 mg/ml Galacton-Plus™ (100×concentrate, Tropix, Bedford, Mass.; stored at 4° C. or optimally at $-20°$ C.) was added to Buffer B, diluted 1:100, immediately before use. Buffer B and the β-galactosidase substrate mixture was preferably used within 24 hours.

2–10 $\mu$L of individual cell extracts or purified enzyme were aliquoted into luminometer sample tubes or microplate wells. If less than 10 $\mu$L of extract was used, lysis solution was added to bring total volume up to 10 $\mu$L to ensure the same concentration of reducing agent and other components is present in each assay sample. The amount of cell extract required varied depending on the level of expression and the instrument used. The concentration of extract was adjusted to keep the signal within the linear range of the assay.

Buffer A (25 $\mu$L) was added to the tubes containing the extract samples. Within 10 minutes of adding Buffer A, 100 $\mu$L of Buffer B was injected into the samples. The light signal produced from the luciferase reaction was measured using a 2 second delay and a 5 second integration.

The samples were incubated for 30–60 minutes at room temperature. Then 100 $\mu$L of accelerator was added. The accelerator contained 100% Sapphire II™ (10 mg/ml polyvinyl benzyl tributyl ammonium chloride) and 0.3 M diethanolamine unbuffered at approximately pH 10.8. After a 2 second delay, the light signal produced from the Galacton-Plus™ and β-galactosidase reaction was measured on a monolight 2010 luminometer (Analytical Luminescence Laboratory, Ann Arbor, Mich.) for 5 seconds.

Figure 2:
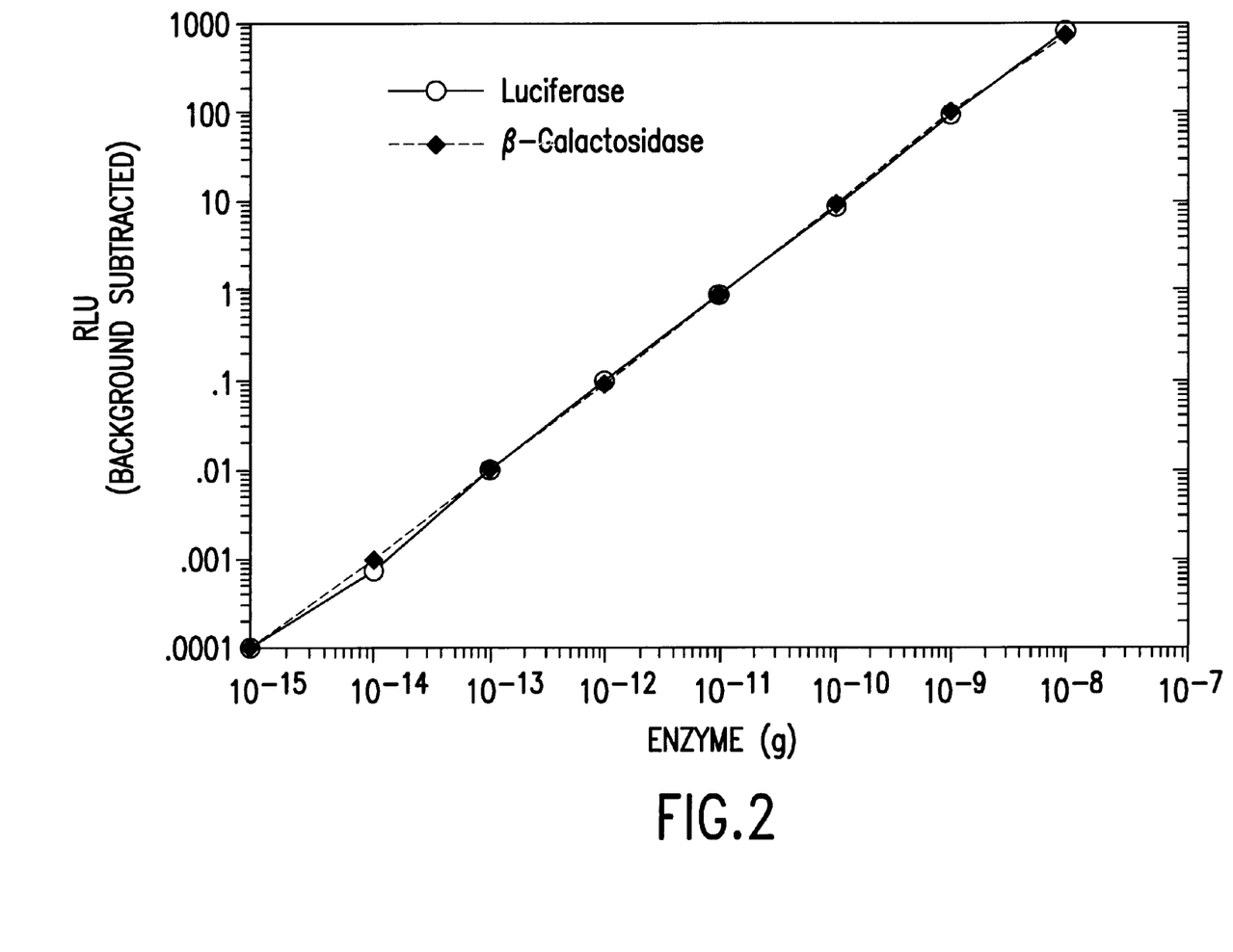
FIG. 2 shows a graph of the detection of luciferase and β-galactosidase according to the methods of the present invention (RLU=relative light unit).

FIG. 2 shows a graph of the relative light units (RLUs) of purified luciferase and β-galactosidase versus the amount of enzyme present. This figure shows that $10^{-15}$ to $10^{-8}$ g of luciferase and β-galactosidase can be detected by the methods of the present invention.

Figure 3:
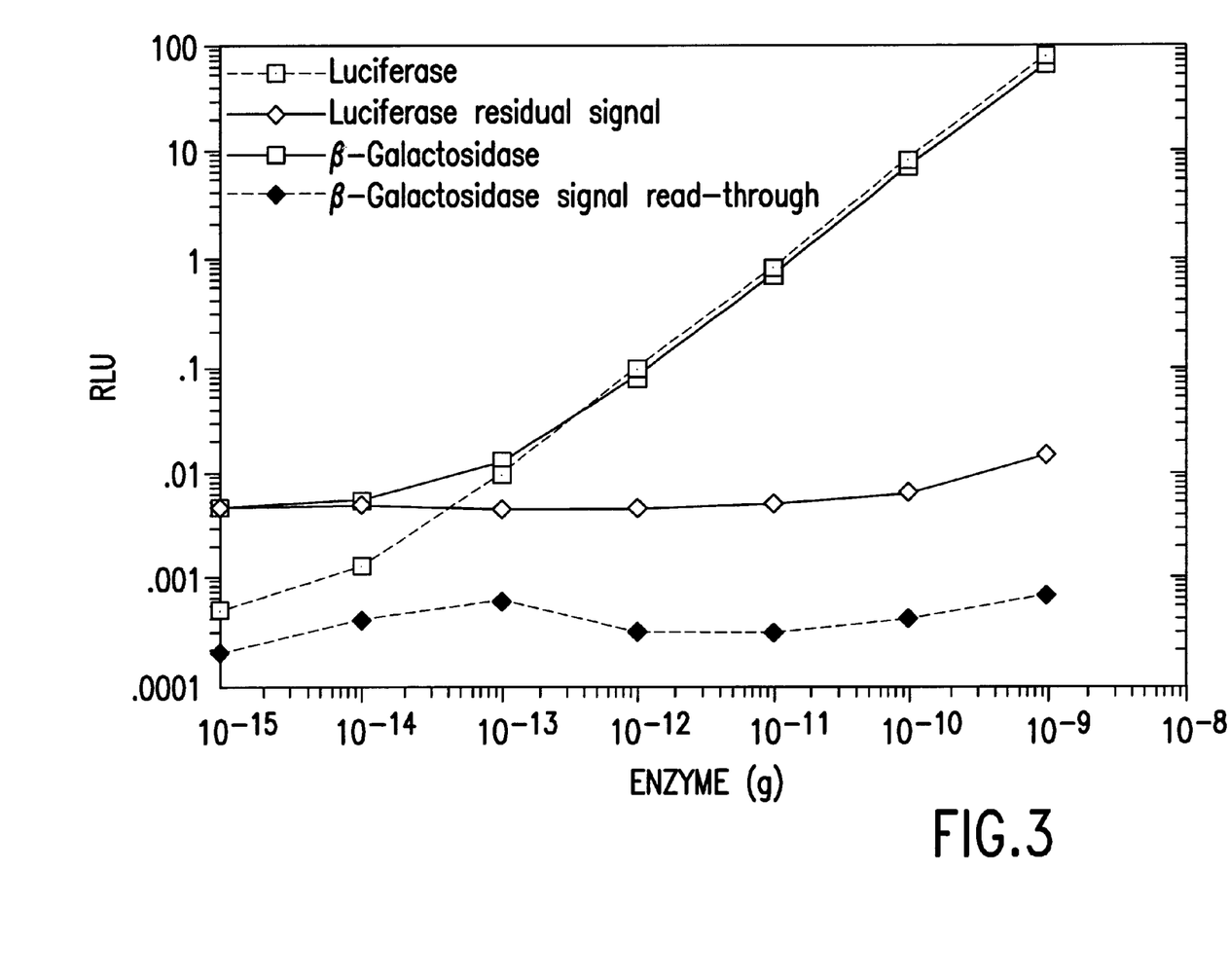
FIG. 3 shows the detection of luciferase and β-galactosidase and the levels of background signal.

The level of interference from one enzyme on the low level detection of the other enzyme was measured by assaying the individual enzyme dilution series for β-galactosidase and luciferase and is shown in FIG. 3. Purified luciferase and β-galactosidase were diluted in cell lysis solution. A set of dilutions of each enzyme was assayed following the protocol as described above. The luciferase curve shows signal intensity following injection of Buffer B into diluted luciferase. The luciferase residual signal curve shows signal intensity following injection of the accelerator into diluted luciferase. The β-galactosidase curve shows the signal intensity following injection of accelerator into diluted β-galactosidase. The β-galactosidase signal readthrough shows the signal intensity following injection of Buffer B into diluted β-galactosidase. The results indicate that when luciferase is not present, levels of βgalactosidase up to 1 ng do not increase the signal from the luciferase portion of the assay over background. When no β-galactosidase is present, quantities of luciferase below 1 ng do not increase the background signal in the βgalactosidase assay. At luciferase levels 1 ng or above, residual luciferase signal is measureable; however, this level of signal would only interfere with very low level detection of βgalactosidase and a dynamic range over 5 orders of magnitude of enzyme concentration is maintained.

EXAMPLE III

Chemiluminescent Assay for Luciferase and β-Glucuronidase Reporter Enzymes

Mammalian cell lysis extracts are prepared as described in Example I. Lysis Buffer A and B, are prepared and stored as described in Example II. The βglucuronidase substrate (Glucuron™, 100×concentrate, Tropix, Bedford, Mass.: stored at −20° C.) is added to Buffer B, diluted 1:100, immediately before use. Buffer B and the Glucuronm™ substrate mixture was preferably used within 24 hours.

2–10 µl of individual cell extracts or purified enzyme diluted in lysis buffer are aliquoted into luminometer sample tubes or microplate wells. If less than 10 µl of extract is used, lysis solution is added to bring total volume up to 10 µl to ensure the same concentration of reducing agent and other components is present in each assay sample.

Buffer A (25 µl) is added to the tubes containing the extract/enzyme samples. Within 10 minutes of adding Buffer A, 100 µl of Buffer B is injected into the samples. The light signal produced from the luciferase reaction is measured using a 2 second delay and a 5 second measurement.

The samples are incubated for 30–60 minutes at room temperature. Then 100 µl of accelerator (0.3M diethanolamine, 10% Sapphire II™) is added. After a 2 second delay, the light signal produced from the β-glucuronidase reaction is measured for 5 seconds.

EXAMPLE IV

Chemiluminescent Assay Procedure for β-Galactosidase and Alkaline Phosphatase Reporter Enzymes Using Two Dioxetane-Containing Substrates Cell lysis solution is prepared to contain 0.1 M potassium phosphate, pH 7.8, 0.2% Triton X-100 as described above. Dithiothrietol (DTT) is added fresh prior to use to a final concentration of 0.5 mM. The cells are rinsed twice with 1×tris buffered saline (TBS) containing: TBS, 0.05 M tris, 0.15 M NaCl, pH7.4. Cell lysis is performed as described above.

The cells are then transferred to a microfuge tube and centrifuged for 2 minutes to pellet any debris. The supernatant is then transferred to a fresh microfuge tube. The cell extracts are either used immediately or frozen at −70° C. for future use.

The cell extract (1–20 µL) is aliquoted into luminometer sample tubes or microplate wells. Reaction buffer (100 µL) containing 0.1 M NaPO$_4$, pH 8.0 and containing Galacton™ (0.025mM) is added to the wells. The sample tubes are incubated for 30 minutes at room temperature.

100 µL of an accelerator solution containing 0.3 M diethanolamine, 10% Sapphire II™ (polyvinyl benzyl tributyl ammonium chloride, 10% w/w) is injected into the sample tubes and after a 2 second delay, the light signal produced from the β-galactosidase reaction was measured for 5 seconds.

After the light signal produced from the Galacton™-β-galactosidase reaction is read, 25–100 µL of CSPD solution was immediately injected into the sample tubes to obtain a final concentration of 0.4 mM CSPD. The samples are incubated for 30 minutes to permit the decay of activated Galacton and for the alkaline phosphatase/CSPD signal to reach a plateau. The light signal produced by decomposition of CSPD by alkaline phosphatase is measured.

Alternatively, the step of incubating the samples for 30 minutes subsequent to the quantification of β-galactosidase is shortened or altogether eliminated as the above assay is performed at higher temperatures. In such a method, the assay is performed at a temperature of 25–40° C.

EXAMPLE V

Chemiluminescent Assay for Luciferase, β-Galactosidase and Alkaline Phosphatase Mammalian cell lysis extracts are prepared as described in Example I. Lysis Buffer and Buffer B are prepared and stored as described in Example II. Buffer A was prepared as in Example II except for the omission of EDTA. The β-galactosidase substrate (Galacton™, 100X concentrate, Tropix, Bedford, Mass.: stored at −20° C.) is added to Buffer B, diluted 1:100, immediately before use. Buffer B and the Galacton™ substrate mixture is preferably used within 24 hours.

2–10 µl of individual cell extracts or purified enzymes diluted in lysis buffer are aliquoted into luminometer sample tubes or microplate wells. If less than 10 µl of extract is used, lysis solution is added to bring total volume up to 10 µl to ensure the same concentration of reducing agent and other components is present in each assay sample.

Buffer A (25 µl) is added to the tubes containing the extract/enzyme samples. Within 10 minutes of adding Buffer A, 100 µl of Buffer B is injected into the samples. The light signal produced from the luciferase reaction is measured using a 2 second delay and 5 second measurement.

The samples are incubated for 30–60 minutes at room temperature. Then 100 µl of accelerator (0.3 M diethanolamine, 10% Sapphire II™) is added. After a 2 second delay, the light signal produced from the β-galactosidase reaction is measured for 5 seconds.

After the light signal produced by the β-galactosidase substrate is read, 25–100 µl of CSPD solution is immediately injected into the sample tubes to obtain a final concentration of 0.4mM CSPD. The samples are incubated for 30 minutes to permit the decay of activated Galacton™ and for the alkaline phosphatase/CSPD signal to reach a plateau. Following this incubation, the light signal produced by decomposition of CSPD by alkaline phosphatase is measured.

The invention has been described in detail with particular references to the preferred embodiments thereof. However, it will be appreciated that modifications and improvements within the spirit and scope of this invention may be made by those skilled in the art upon considering the present disclosure.

We claim:

1. A method of assaying enzyme-mediated luminescent reactions, comprising:
    (a) initiating a first enzyme-mediated luminescence reaction;
    (b) quantifying luminescence produced by said luminescent reaction;
    (c) quenching luminescence from said enzyme-mediated luminescence reaction;
    (d) initiating a second enzyme-mediated luminescence reaction distinct from said first enzyme-mediated luminescence reaction; and
    (e) quantifying luminescence produced by said second enzyme-mediated luminescence reaction.

2. The method of claim 1, wherein said quenching step is achieved by introducing at least one quench reagent to the luminescence reaction.

3. The method of claim 1, wherein at least one of the luminescence reactions is a luciferase-mediated luminescence reaction.

4. The method of claim 1, which comprises adding an accelerator solution which substantially inactivates said first enzyme-mediated reaction and simultaneously increases the luminescent signal produced by said second enzyme-mediated luminescence reaction.

5. A kit for conducting enzyme-mediated luminescent reaction assays, comprising:
   a first enzyme substrate which, when reacted with an enzyme in an aqueous environment, produces a luminescent signal;
   a reagent which is capable of reducing said luminescent signal by decreasing the activity of said enzyme; and
   a second enzyme substrate different from said first substrate which is caused to emit a luminescent signal by contact with a second enzyme.

6. The kit of claim 5, wherein said first substrate is luciferin and said second substrate is a dioxetane bearing a galactopyranoside moiety, the cleavage of which by a β-galactosidase enzyme causes said dioxetane to decompose and emit a luminescent signal.

* * * * *